US008728033B2

(12) United States Patent
Watanabe et al.

(10) Patent No.: US 8,728,033 B2
(45) Date of Patent: May 20, 2014

(54) PHARMACEUTICAL INJECTION DEVICE

(75) Inventors: Atsushi Watanabe, Ehime (JP); Seiji Kikuchi, Ehime (JP); Tsuguhiro Kondoh, Ehime (JP); Toshiaki Ilo, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 0 days.

(21) Appl. No.: 13/581,014

(22) PCT Filed: Feb. 23, 2011

(86) PCT No.: PCT/JP2011/001006
§ 371 (c)(1),
(2), (4) Date: Aug. 24, 2012

(87) PCT Pub. No.: WO2011/108225
PCT Pub. Date: Sep. 9, 2011

(65) Prior Publication Data
US 2012/0323176 A1    Dec. 20, 2012

(30) Foreign Application Priority Data
Mar. 1, 2010 (JP) ................................. 2010-043932

(51) Int. Cl.
*A61M 5/31*    (2006.01)
*A61M 5/20*    (2006.01)
(52) U.S. Cl.
USPC .......................................... 604/131; 604/151

(58) Field of Classification Search
USPC .................... 604/67, 131, 151–152, 154–155
See application file for complete search history.

(56) References Cited

U.S. PATENT DOCUMENTS 4,978,335 A * 12/1990 Arthur, III ....................... 604/67
5,383,858 A    1/1995 Reilly et al.
(Continued)

FOREIGN PATENT DOCUMENTS

CN    101641125    2/2010
JP    2-128950    10/1990
(Continued)

OTHER PUBLICATIONS

International Search Report issued Apr. 19, 2011 in International (PCT) Application No. PCT/JP2011/001006.
(Continued)

*Primary Examiner* — Quynh-Nhu H Vu
(74) *Attorney, Agent, or Firm* — Wenderoth, Lind & Ponack, L.L.P.

(57) ABSTRACT

The pharmaceutical injection device of the present invention comprises an inner case (111) in which is mounted a preparation syringe (104) having an identification code (104*a*), a piston driving motor (115) that drives the preparation syringe (104) mounted in this inner case (111), and a code reader (112) that reads the identification code (104*a*) of the preparation syringe (104). A slide motor (113) is provided that drives the preparation syringe (104) mounted in the inner case (111) and/or the code reader (112), so that the identification code (104*a*) is read by the code reader (112).

9 Claims, 13 Drawing Sheets

(56) References Cited

U.S. PATENT DOCUMENTS

| | | | |
|---|---|---|---|
| 5,741,232 A | 4/1998 | Reilly et al. | |
| 5,795,333 A | 8/1998 | Reilly et al. | |
| 5,997,502 A | 12/1999 | Reilly et al. | |
| 6,019,745 A * | 2/2000 | Gray | 604/131 |
| 6,090,064 A | 7/2000 | Reilly et al. | |
| 6,402,717 B1 | 6/2002 | Reilly et al. | |
| 6,475,192 B1 | 11/2002 | Reilly et al. | |
| 6,562,008 B1 | 5/2003 | Reilly et al. | |
| 6,733,478 B2 | 5/2004 | Reilly et al. | |
| 7,686,789 B2 * | 3/2010 | Nemoto et al. | 604/246 |
| 8,366,671 B2 * | 2/2013 | Neer | 604/151 |
| 8,409,138 B2 | 4/2013 | James et al. | |
| 2003/0060768 A1 * | 3/2003 | Kiyatake et al. | 604/154 |
| 2009/0156931 A1 * | 6/2009 | Nemoto et al. | 600/432 |
| 2010/0049125 A1 | 2/2010 | James et al. | |

FOREIGN PATENT DOCUMENTS

| | | |
|---|---|---|
| JP | 4-113483 | 4/1992 |
| JP | 5-500917 | 2/1993 |
| JP | 6-154322 | 6/1994 |
| JP | 2000-89386 | 3/2000 |
| JP | 2003-83985 | 3/2003 |
| JP | 2004-313579 | 11/2004 |
| JP | 2005-338938 | 12/2005 |
| JP | 2007-185288 | 7/2007 |

OTHER PUBLICATIONS

Chinese Office Action issued Oct. 12, 2013 in corresponding Chinese Application No. 201180011601.7.

* cited by examiner

US 8,728,033 B2

PHARMACEUTICAL INJECTION DEVICE

TECHNICAL FIELD

The present invention relates to a pharmaceutical injection device to which is mounted a preparation syringe containing a preparation, and which is able to inject a preparation into an organism, etc., and more precisely relates to a pharmaceutical injection device that automatically identifies a mounted preparation.

BACKGROUND ART

With conventional pharmaceutical injection devices of this type, a configuration such as the following was employed in order to determine whether or not a drug was suitable for injection into a test subject.

Specifically, a conventional pharmaceutical injection device comprised a mounting portion to which was mounted a preparation syringe having an identification code, an injection driver for driving a preparation syringe mounted to this mounting portion, and reading section for reading the identification code of the preparation syringe (see Patent Literature 1, for example).

CITATION LIST

Patent Literature

Patent Literature 1: Japanese Laid-Open Patent Application H6-154322

SUMMARY

With a conventional pharmaceutical injection device, a reading section is provided, to the mounting portion. Therefore, when the user mounts the preparation syringe to the mounting portion, the identification code provided to the preparation syringe is read by the reading section.

However, since the reading of the identification code is reliant on the operation in which the user mounts the preparation syringe to the mounting portion, there is the risk that the identification code cannot be read, depending on this mounting operation. Thus, the user ends up having to repeat the mounting operation a number of times, and it is often the case that the identification code is read again, making this pharmaceutical injection device extremely inconvenient to use.

In view of this, it is an object of the present invention provide a pharmaceutical injection device that is more convenient to use in identifying the type of preparation syringe that is mounted.

Solution to Problem

To achieve this object, the pharmaceutical injection device pertaining to the present invention comprises a mounting portion, an injection driver, reading section, and read driving section. A preparation syringe having an identification code is mounted to the mounting portion. The injection driver drives a preparation syringe mounted to the mounting portion. The reading section reads an identification code on the preparation syringe. The read driving section drives the preparation syringe mounted to the mounting portion and/or the reading section, so that the identification code is read by the reading section.

Advantageous Effects

Because of the above-mentioned constitution, the present invention can provide a pharmaceutical injection device that is extremely convenient to use in identifying the type of preparation syringe.

Specifically, with the present invention, an identification code is read by the reading section by driving the preparation syringe and/or the reading section after this preparation syringe has been mounted to the mounting portion. Accordingly, to read an identification code, there is no need for the preparation syringe to be mounted a number of times to the mounting portion, which means that a pharmaceutical injection device that is extremely convenient to use can be provided.

DESCRIPTION OF EMBODIMENTS

Embodiments of the present invention will now be described in detail through reference to the drawings.

Embodiment 1

Figure 1:
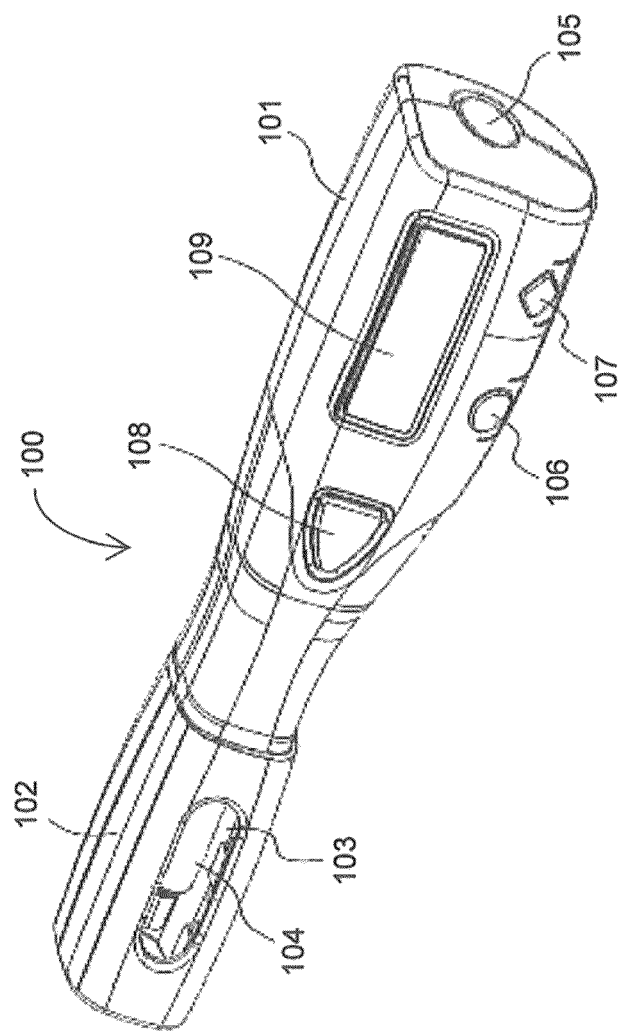
FIG. 1 is an oblique view of the configuration of the pharmaceutical injection device pertaining to an embodiment of the present invention.
Figure 2:
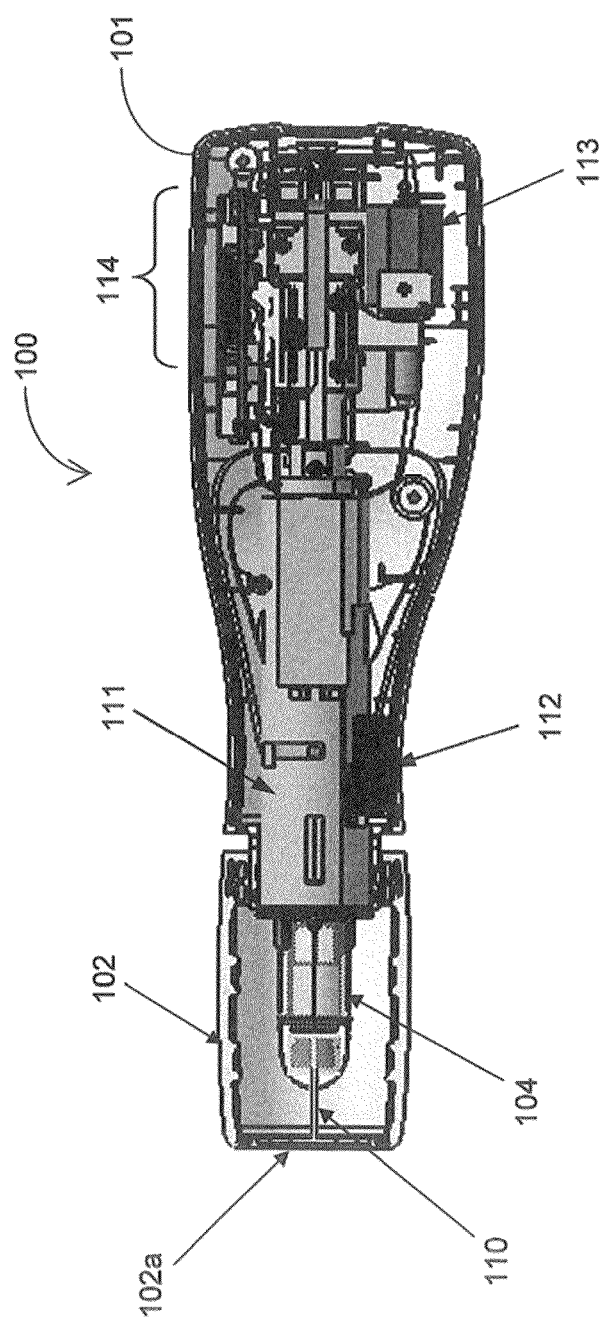
FIG. 2 is a see-through plan view illustrating the internal configuration of the pharmaceutical injection device in FIG. 1.

As shown in FIGS. 1 and 2, a pharmaceutical injection device 100 in this embodiment comprises a housing 101 that is rectangular in shape and is held in the hand, and a distal end cap 102 that is mounted to the distal end side of the housing 101. An elliptical confirmation window 103 is provided to the outer peripheral face of the distal end cap 102. Also, a power button 105, an air bleed button 106, a finish button 107, a pharmaceutical injection button 108, and a display section 109 an example of a notification section) are provided to the outer peripheral face of the housing 101.

In FIG. 1, a state is shown in which a preparation syringe 104 has been mounted to the pharmaceutical injection device 100. The mounting state of the preparation syringe 104 can be confirmed by looking at the preparation syringe 104 through the confirmation window 103.

The distal end cap 102 can be removably attached to the distal end of the housing 101 and, as shown in FIG. 2, is used when mounting or removing the preparation syringe 104 to or from an inner case 111 (an example of a mounting portion) inside the housing 101, and when attaching or removing an injection needle 110 for injecting a pharmaceutical solution to or from the preparation syringe 104.

As discussed above, the distal end cap 102 has the confirmation window 103 for checking the interior. Therefore, whether there is a preparation syringe 104, what type it is, how much preparation remains, and so forth can be confirmed visually.

The distal end cap 102 also serves as a cover so that the distal end of the injection needle 110 used for preparation injection will not be exposed from the distal end portion of the distal end cap 102. Furthermore, during preparation injection, the distal end face of the distal end cap 102 is brought into contact with the skin, and the injection needle 110 is moved toward and away from the skin through a distal end opening 102a in the front face of the distal end cap 102. In this state, the injection needle 110 punctures the skin and the preparation inside the preparation syringe 104 is injected into the body.

That is, the distal end cap 102 is provided to cover any sharp parts with a pointed distal end, such as the injection needle 110, and to ensure safe usage.

As discussed above, the confirmation window 103 is used to check the interior, to visually confirm whether there is a preparation syringe 104, what type it is, how much preparation remains, and so forth. The confirmation window 103 may be formed as an uncovered opening, or a transparent cover may be mounted to the opening. That is, the important thing is that the interior of the distal end cap 102 can be visually checked through the confirmation window 103.

The power button 105 is provided to the end of the housing 101, and is used to switch the power on and of to the pharmaceutical injection device 100.

The air bleed button 106 is used to bleed off the air inside the preparation syringe 104. That is, prior to injecting the preparation contained in the preparation syringe 104, air is sometimes trapped in the preparation syringe 104 or in the injection needle 110 (a hollow needle) used for injection. Therefore, if this happens, the air bleed button 106 is pressed to drive the piston drive motor 115 shown in FIG. 4 (an example of an injection driver), and a piston unit 116 pushes out the air to the outside of the preparation syringe 104 and the injection needle 110.

The finish button 107 is pressed when proceeding to the next step after performing air bleed-off with the air bleed button 106 or after checking the display on the display section 109 is finished.

The pharmaceutical injection button 108 is pressed to inject a pharmaceutical after preparations for injecting a pharmaceutical have been finished. When the pharmaceutical injection button 108 is pressed, as discussed above, the injection needle 110 punctures the skin and the preparation inside the preparation syringe 104 is injected into the body.

The display section 109 is used to display various kinds of necessary information, such as the dosage of the pharmaceutical, the remaining charge of a rechargeable battery 125a installed in the interior (see FIG. 5), and air bleeding, and is constituted by an LCD or an organic EL device.

Next, the internal configuration of the pharmaceutical injection device 100 in this embodiment will be described through reference to FIG. 2.

As shown in FIG. 2, the inner case 111 is provided inside the housing 101. The preparation syringe 104 is mounted inside the inner case 111 as discussed above.

A slide motor 113 is a read driving section for adjusting the positional relation between a code reader 112 and an identification code 104a provided to the preparation syringe 104, and in this embodiment it moves the preparation syringe 104 side.

A position detector 114 detects whether or not a specific position has been reached in the movement of the slide motor 113.

Figure 3:
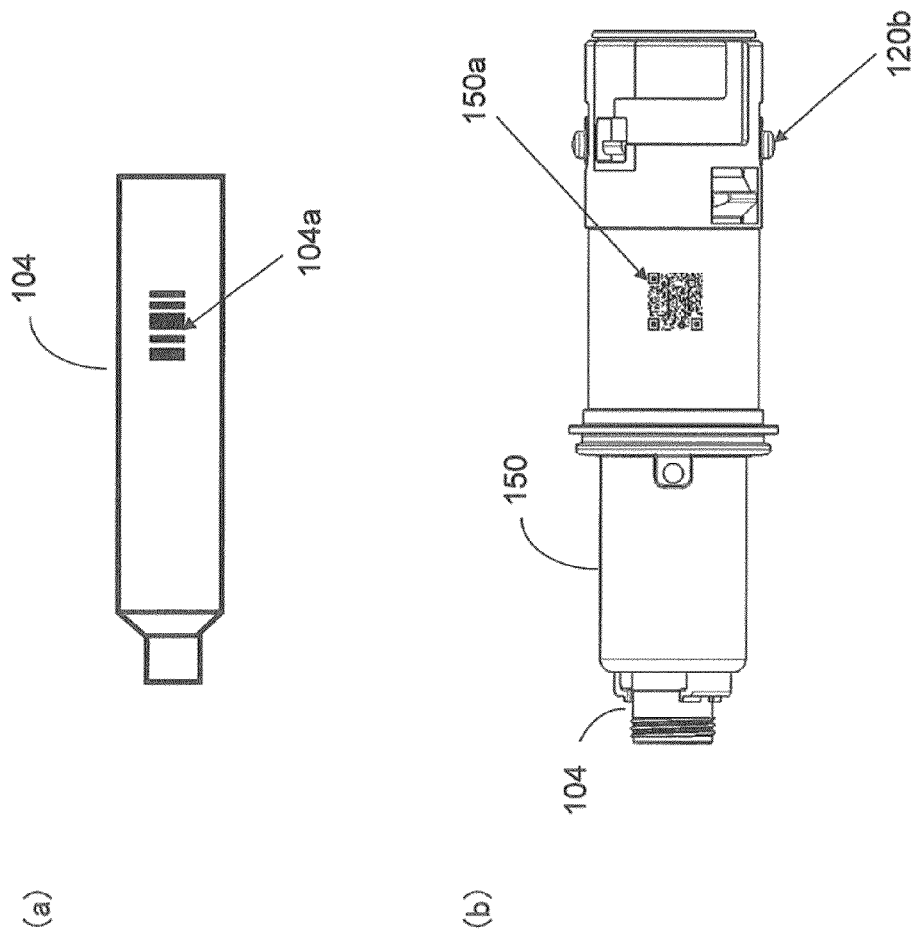
FIG. 3a is a plan view of the preparation syringe of the pharmaceutical injection device in FIG. 1.
FIG. 3b is a plan view of another preparation syringe.

Next, the identification code of the preparation syringe 104 will be described through reference to FIG. 3.

As shown in FIG. 3a, the preparation Syringe 104 is in the form of a slender cylinder, and a one-dimensional bar code is affixed as the identification code 104a to the outer peripheral face toward the rear of the cylinder. The identification code 104a includes, for example, the preparation name, preparation code, manufacturer's name, manufacture date, place of manufacture, lot number, expiration date, destination, and other such information.

The identification code 104a may also be a barcode printed directly on the preparation syringe 104. Taking into account the conditions for the identification code 104a, a label is more stable than a directly printed barcode. This is because the preparation syringe 104 is made from transparent glass or another such material, so if the barcode is printed directly, there will he problems such as letting light through, or scattering and reflecting light since there is surface gloss. Thus, it is preferable to use a barcode printed on an opaque label as the identification code 104a.

Also, in FIG. 3a the barcode is disposed in the axial direction of the preparation syringe 104, but the present invention is not limited to this, and the barcode may be disposed in a direction perpendicular to the axial direction (the peripheral direction of the preparation syringe 104).

The identification code 104a may be a one-dimensional barcode or a two-dimensional barcode. Examples of one-dimensional barcode include JAN (EAN, UPC), ITF, Code 39, NW-7, and Code 128.

As for two-dimensional barcode, PDF417 and Code 49 are typical as stacked two-dimensional barcode, while QR code, Data Matrix, Vericode, and the like are typical as matrix-type two-dimensional barcode.

Figure 4:
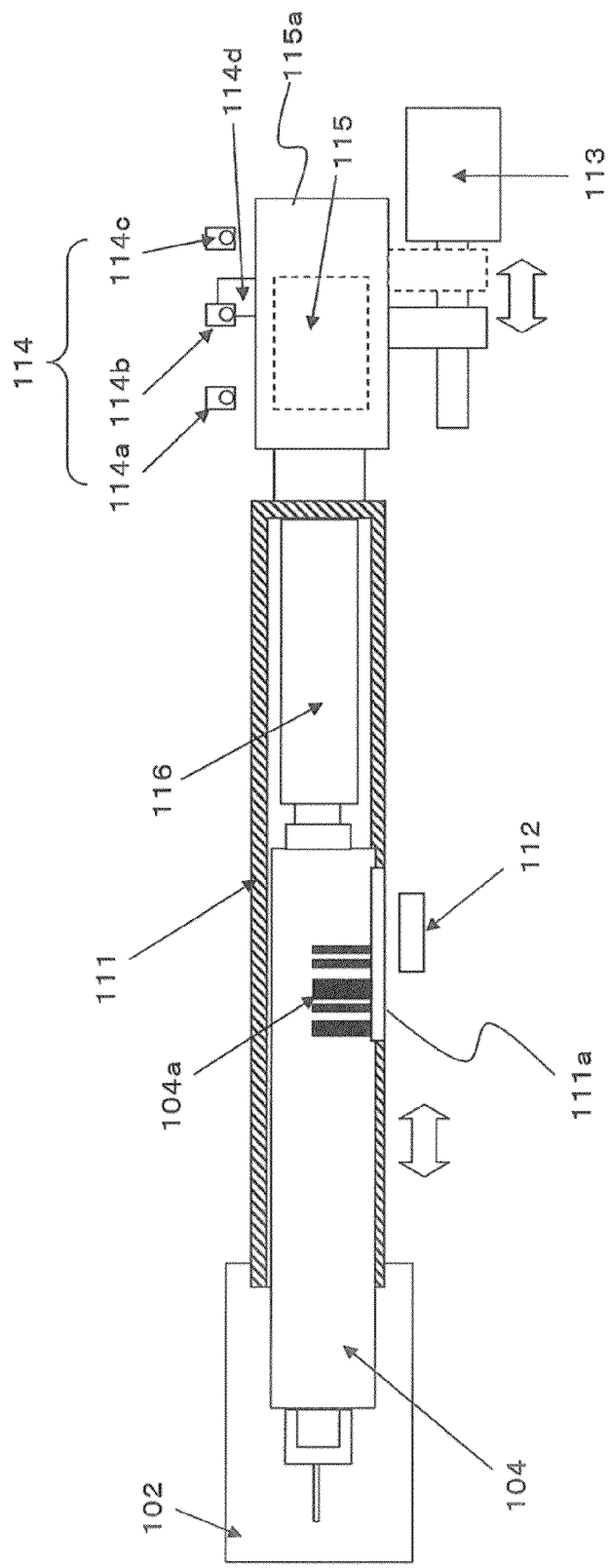
FIG. 4 is a cross section of the main components of the pharmaceutical injection device in FIG. 1.

As discussed above, the identification code 104a provided to the outer peripheral lace of the preparation syringe 104 is read by the code reader 112 (an example of a reading section) in the outer peripheral direction of the inner case 111, as shown in FIGS. 2 and 4. To perform this reading, an opening 111a that is longer than the identification code 104a is formed in the lengthwise direction of the outer peripheral face of the cylindrical inner case 111, which is open on the distal end side.

As shown in FIG. 4, the slide motor 113 is a read driving section for adjusting the positions of the code reader 112 and the identification code 104a provided to the preparation syringe 104. Driving this slide motor 113 moves the piston drive motor 115 and the inner case 111 integrally forward and backward. This allows the code reader 112 and the identification code 104a to be positioned.

When the slide motor 113 is driven, the piston drive motor 115 and the inner case 111 move forward and backward integrally At this point the piston unit 116 is not driven forward and backward with respect to the preparation syringe 104.

The time when the piston unit 116 moves forward and backward with respect to the preparation syringe 104 is when the piston drive motor 115 is driven.

Meanwhile, the position detector 114 disposed at a specific spacing near he piston drive motor 115 detects, along with the inner case 111, the position to which the piston drive motor 115 has been moved by the slide motor 113.

As shown in FIG. 3b, in a state in which the preparation syringe 104 has been mounted in a dedicated cartridge 150, an identification code 150a should be provided on the outer peripheral face of the dedicated cartridge 150.

Also, as shown in FIG. 3b, QR code is used instead of barcode for the identification code 150a. Accordingly, in this case the code reader 112 shown in FIG. 4 should also be changed to one that can read the identification code 150a.

When a dedicated cartridge 150 such as this is used, the inner case 111 shown in FIG. 4 should be changed to one with a larger diameter in order to mount this dedicated cartridge 150.

In this case, the dedicated cartridge 150 can be fixed to the inner case 111 by engaging protrusions 120b in recesses (not shown) in the large-diameter inner case 111.

The following description is for a case in which just the preparation syringe 104 shown in FIG. 3a is mounted by itself.

The distal end cap 102 in FIG. 4 is mounted and fixed to the housing 101 of the pharmaceutical injection device 100 as shown in FIGS. 1 and 2.

The inner case 111 is able to slide forward and backward (the left and right directions indicated by the arrows in FIG. 4) inside the housing 101 and inside the distal end cap 102, houses the piston unit 116 in its interior toward the rear, and can push the pharmaceutical in the preparation syringe 104 forward and out.

The position of the preparation syringe 104 is restricted with respect to the inner case 111 (is removably fixed when mounted). Consequently it is mounted at a position where the identification code 104a can he read by the code reader 112.

The identification code 104a can be read in the lengthwise direction of the preparation syringe 104.

The position detector 114 is configured so as to include reflecting or transmitting photosensors 114a to 114c disposed at three places at a specific spacing.

Of these, the photosensor 114a detects whether or not the inner case 111 is in the needle insertion position. The photosensor 114b detects whether or not the inner case 111 is in the needle retraction position. The photosensor 114c detects whether or not the inner case 111 is in the identification code 104a reading position.

A blocker plate 114d blocks or transmits light to the photosensors 114a to 114c during forward and backward sliding, which allows the position of the inner case 111 to be detected. Also, the blocker plate 114d is formed, integrally with a case 115a that houses the piston drive motor 115. The case 115a is connected to the inner case 111 and the slide motor 113, and can be slid in the forward and backward direction by the rotation of the slide motor 113.

The method for reading the identification code 104a configured as above will now be described.

In FIG. 4, the inner case 111 is stopped at a position where the photosensor 114b is blocked off by the blocker plate 114d, that is, at the needle retraction position. Here, if it is detected that the preparation syringe 104 has been mounted to the inner case 111, and the distal end cap 102 has been mounted to the housing 101, the drive of the slide motor 113 slides the blocker plate 114d backward so that it stops at a position where the photosensor 114c is blocked oils.

After this, the slide motor 113 is reversed and the blocker plate 114d is slid forward and stops at a position where the photosensor 114b is blocked off.

In reciprocal operation in the forward and backward direction (the axial direction of the preparation syringe 104), the code reader 112 reads the identification code 104a on the preparation syringe 104 through the opening 111a, and determines whether or not the proper preparation syringe 104 has been mounted in the inner case 111. If it is determined that the proper preparation syringe 104 has been mounted, injection of the pharmaceutical becomes possible. On the other hand, if the wrong preparation syringe 104 has been mounted, the display section 109 displays an error message, and a state in which no pharmaceutical can he injected results. If the wrong identification code is read, the inner case 111 in which the preparation syringe 104 has been mounted is moved once more in the forward and backward (retry). This prevents incorrect detection attributable to an improper mounting state, and improves reading accuracy. It is also possible to read the identification code twice in a single operation by reading the identification code once in the forward operation and once in the backward operation.

Figure 5:
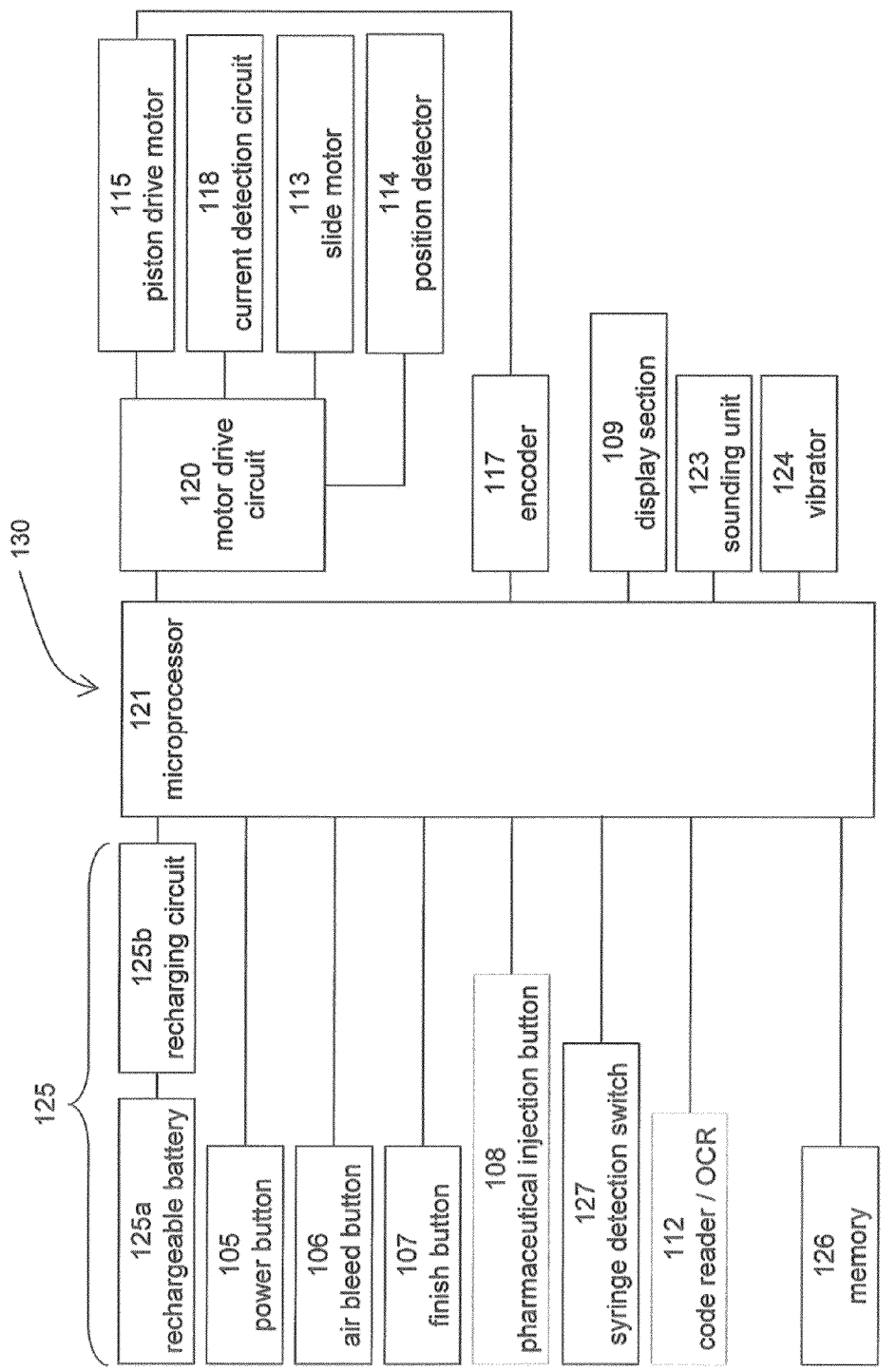
FIG. 5 is an electrical block diagram of the pharmaceutical injection device in FIG. 1.

FIG. 5 shows an electrical block diagram of an electrical circuit 130 (including the peripheral portions) inside the pharmaceutical injection device 100 in this embodiment. A power supply 125 is constituted by the rechargeable battery 125a and a recharging circuit 125b. Consequently, power is supplied to all parts of the pharmaceutical injection device 100, including a microprocessor 121.

The microprocessor 121 is connected to the above-mentioned power button 105, the air bleed button 106, the finish button 107, the pharmaceutical injection button 108, a syringe detection switch 127, the code reader 112 that reads the identification code 104a, a memory 126, a motor drive circuit 120, an encoder 117, the display section 109, a sounding unit 123, and a vibrator 124.

The motor drive circuit 120 is connected to the piston drive motor 115, a current detection circuit 118, the slide motor 113, and the position detector 114.

The syringe detection switch 127 detects whether or not the preparation syringe 104 has been mounted in the proper state inside the inner case 111.

The memory 126 stores for example, control information such as the dosage in which to inject the preparation inside the preparation syringe 104, as well as injection history information about the preparation that was actually injected, and so forth.

The motor drive circuit 120 is provided to drive the piston drive motor 115 and the slide motor 113.

The current detection circuit 118 detects, on the basis of the amount of current, whether or not the piston drive motor 115 or the slide motor 113 has been driven properly.

The encoder 117 detects the rotational direction and rotational speed of the piston drive motor 115, and controls the dosage of the preparation.

When, for example, the syringe detection switch 127 detects that the preparation syringe 104 has not been properly mounted inside the inner case 111, an error message is displayed on the display section 109 and the sounding unit 123 and the vibrator 124 emit a warning.

Figure 6:
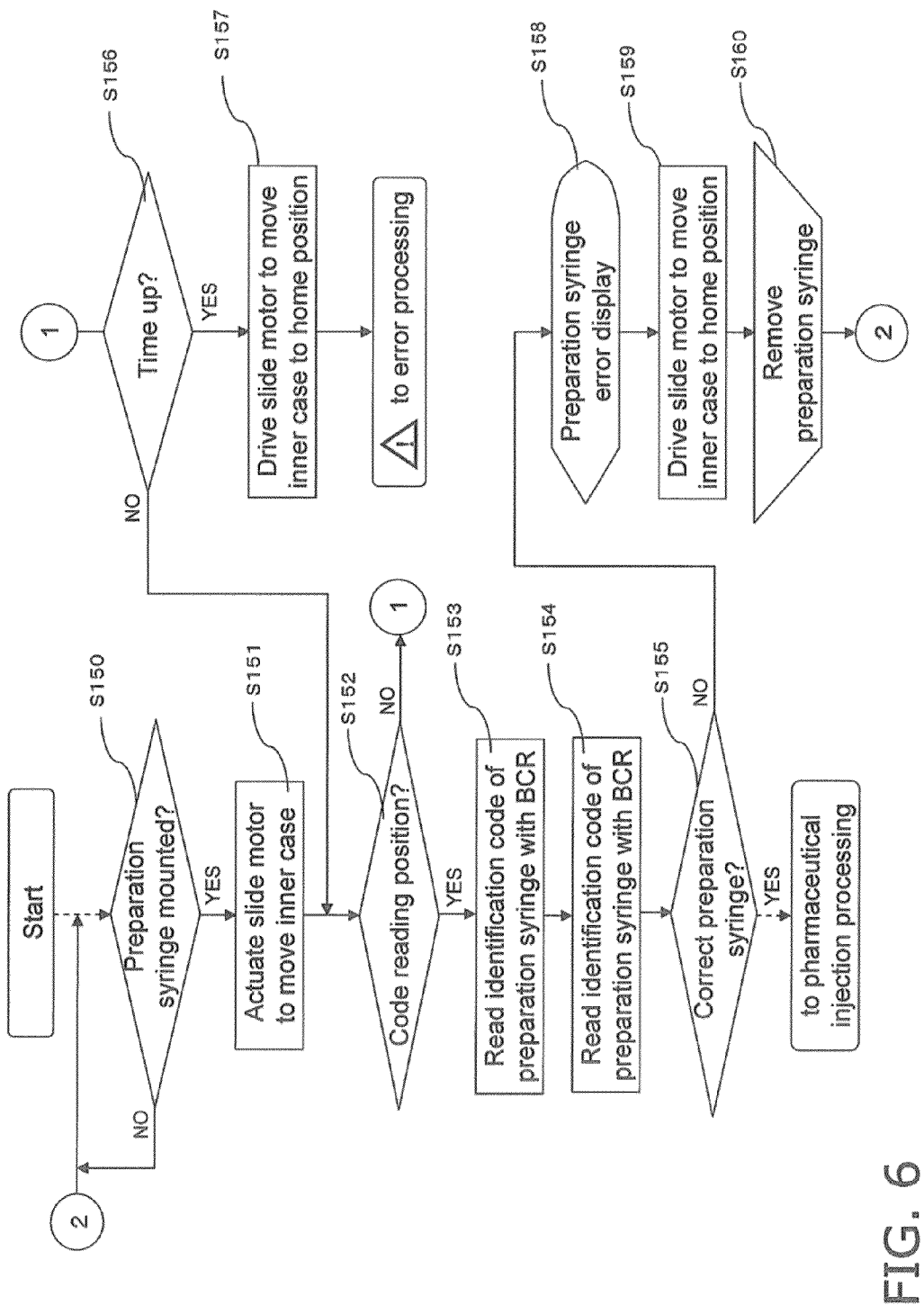
FIG. 6 is a flowchart of the pharmaceutical injection device in FIG. 1.

FIG. 6 is a flowchart of the main operations.

First, in step S150, the syringe detection switch 127 determines whether the preparation syringe 104 has been mounted in the inner case 111.

If the preparation syringe 104 has been mounted properly, the slide motor 113 is actuated in step S151. This allows the inner case 111 to be operated in the forward and backward direction.

Next, in step S152 the position detector 114 determines whether or not the code reading position has been reached.

If it is determined that the code reading position has been reached here, in step S153 the identification code 104a of the preparation syringe 104 is read by the code reader 112. Actually, as discussed above, the blocker plate 114d is slid backward by the drive of the slide motor 113 and stops temporarily at a position where the photosensor 114c is blocked off After this, the slide motor 113 is reversed to slide the blocker plate 114d forward and stop it at a position where the photosensor 114b is blocked off, in this reciprocal operation in the forward and backward direction (the axial direction of the preparation syringe 104), the code reader 112 reads the identification code 104a on the preparation syringe 104 through the opening 111a. In this embodiment, the identification code 104a is again read by the code reader 112 in step S154. Consequently, there are opportunities to read the identification code 104a twice during the forward and backward reciprocation, and reading accuracy can be improved by comparing the two identification codes 104a thus acquired. Naturally, the identification code 104a may instead be read only once.

In step S155, the microprocessor 121 compares the information read from the identification code 104a of the preparation syringe 104 with criteria stored in the memory 126, and if the preparation syringe 104 is the proper one, the flow proceeds to the pharmaceutical injection step, and pharmaceutical injection processing is performed.

Specifically, the slide motor 113 is driven to move the inner case 111 the forward side, and to move the injection needle 110 from the distal end opening 102a to ahead of the distal end cap 102, thereby inserting, the needle into the body.

The reading of the identification code can be carried out together with preparatory operations prior to the pharmaceutical injection, such as air bleeding, which shortens the time it takes to give an injection. The preparation syringe being evaluated here is not limited to containing a single preparation, and may instead contain a plurality of preparations. In this case the types of preparations in the preparation syringe should also be identified.

Next, the piston drive motor 115 is driven to move the piston unit 116 forward. Consequently, the preparation s injected from the preparation syringe 104 into the body, through the injection needle 110, in the amount stored in the memory 126.

In the above procedure, the flow moves to step S156 if it cannot be determined whether or not the code reading position has been reached in step S152. If reading is impossible and time runs out in step S156, the flow moves to step S157. On the other hand, if time does not run out, the flow returns to step S152.

In step S157 the slide motor 113 is driven to move the inner case 111 backward to its original position. After this, error processing is performed, such as displaying an error message on the display section 109.

If it is determined in step S155 that the preparation syringe 104 is not the proper one, an error message is displayed on the display section 109 in step S158. After this, in step S159 the slide motor 113 is driven to move the inner case 111 backward to its original position. In step S160 the preparation syringe 104 is then removed from the inner case 111, the flow returns to step S150, and the procedure is started over from the work of mounting another preparation syringe 104.

Embodiment 2

Figure 7:
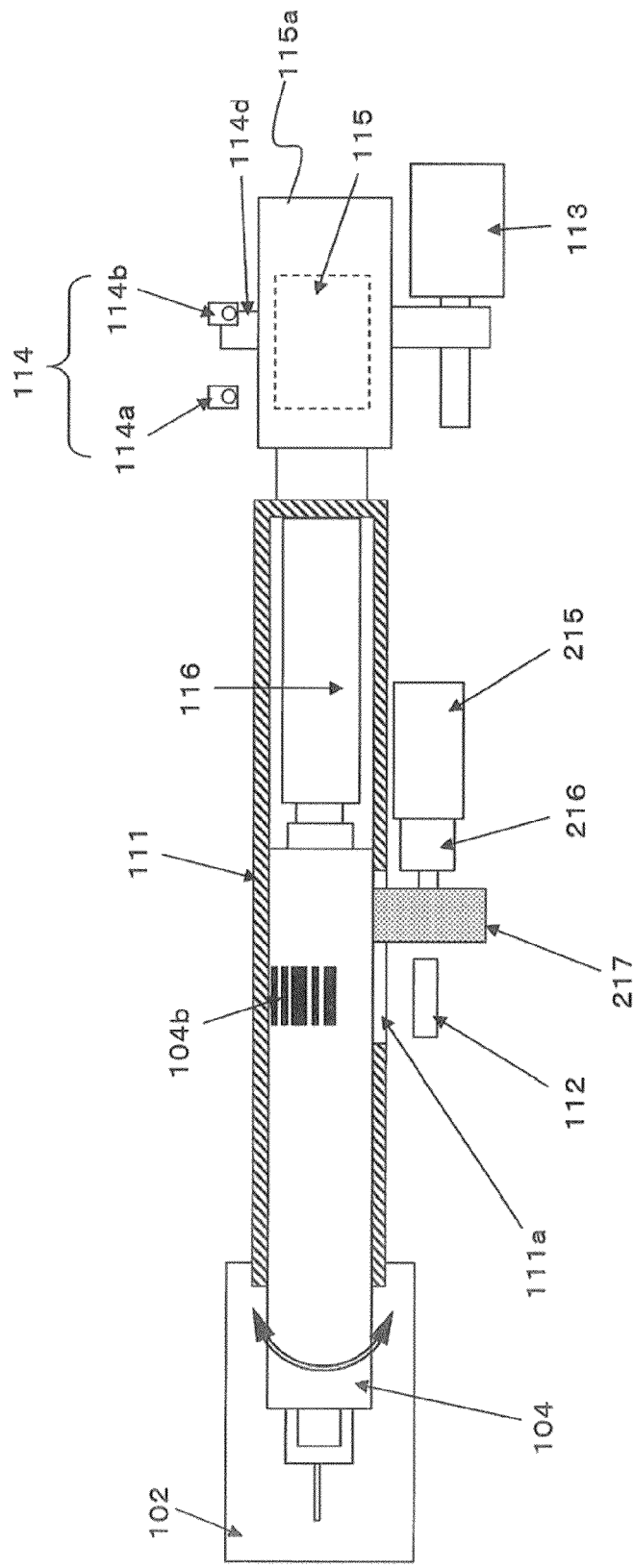
FIG. 7 is a cross section of the main components of the pharmaceutical injection device pertaining to Embodiment 2 of the present invention.

FIG. 7 shows the configuration of the pharmaceutical injection device pertaining to Embodiment 2 of the present invention. Those components in FIG. 7 that are the same as those in FIGS. 1 to 6 will he numbered the same and will not be described again.

Embodiment 2 differs from Embodiment 1 above in that the preparation syringe 104 is held rotatably in the peripheral direction inside the inner case 111, and is mounted at a position where an identification code 104b can be read by the code reader 112.

The identification code 104b is formed by printing along the outer peripheral direction of the preparation syringe 104, or by affixing a printed label, so that the identification code 104b can be read in the rotational direction of the preparation syringe 104.

The position detector 114 uses the photosensor 114a to detect whether or not the inner case 111 is in the needle insertion position. The photosensor 114b, meanwhile, detects whether or not the inner case 111 is in the needle retraction position.

The blocker plate 114d detects the position of the inner case 111 by blocking or transmitting light to the two photosensors 114a and 114b during sliding, in the forward and backward direction.

A syringe drive motor 215 is fixed outside the outer periphery of the inner case 111, and has a speed reducer 216 and a roller 217.

The roller 217 is made from a resilient material, such as rubber or sponge. The roller 217 lightly touches the outer periphery of the power button preparation syringe 104 through the opening 111a in the inner case 111, and rotates the preparation syringe 104 by the drive of the syringe drive motor 215.

The method for reading the identification code 104b configured as above will now be described.

The inner case 111 stops at a position where the photosensor 114b is blocked of by the blocker plate 114d, that is, at the needle retraction position.

Here, if the syringe detection switch 127 detects that the preparation syringe 104 has been mounted to the inner case 111, and the distal end cap 102 has been mounted to the housing 101, the syringe drive motor 215 is driven and the roller 217 rotates via the speed reducer 216. This allows the preparation syringe 104 to be rotated through its contact with the roller 217 (rotation in the direction of the arrow shown in FIG. 7).

At this point the code reader 112 reads the identification code 104b on the preparation syringe 104 through the opening 111a. It is determined whether or not the proper preparation syringe 104 has been mounted, and injection of the pharmaceutical becomes possible if the mounted preparation syringe 104 is the proper one. On the other hand, if the mounted preparation syringe 104 is not the proper one, an error message is displayed on the display section 109 and a state in which no pharmaceutical can be injected results.

To read the identification code 104b more accurately, the identification code 14b may be read by the code reader 112 while the preparation syringe 104 is rotated a few times.

Embodiment 3.

Figure 8:
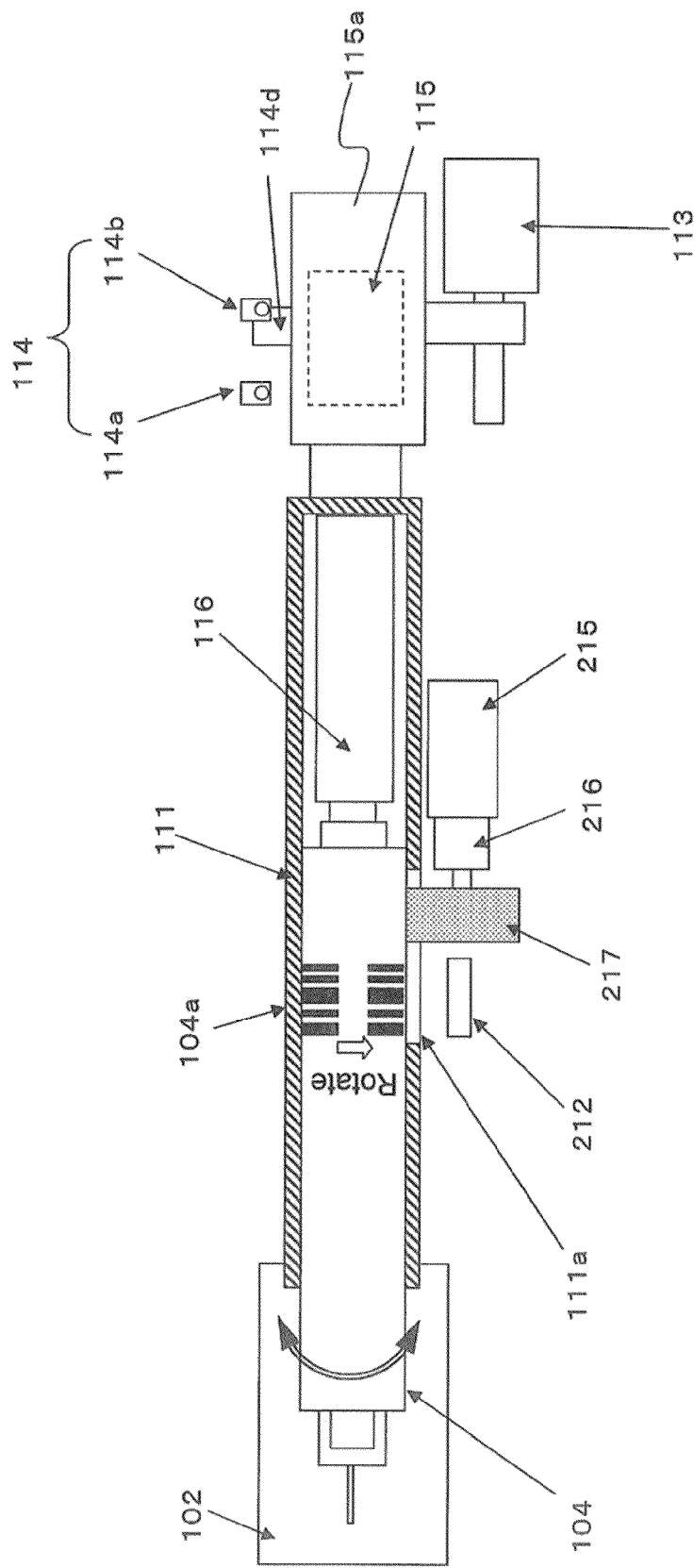
FIG. 8 is a cross section of the main components of the pharmaceutical injection device pertaining to Embodiment 3 of the present invention.

Next, FIG. 8 shows the configuration of the pharmaceutical injection device pertaining to Embodiment 3. Those components in FIG. 8 that are the same as those in FIG. 7 will be numbered the same and will not be described again.

This embodiment differs from Embodiments 1 and 2 above in that a self-propelled code reader 212 is used, as shown in FIG. 8.

That is, the code reader 212 reads the identification code 104a by moving back and forth repeatedly over a specific range in the axial direction of the preparation syringe 104. This improves the accuracy of reading the identification code 104a.

Also, the identification code 104a displayed in the axial direction of the preparation syringe 104 can be read by thus moving the code reader 112 back and forth repeatedly over a specific range in the axial direction of the preparation syringe 104.

The preparation syringe 104 here rotates when the rotational drive force of the syringe drive motor 215 is transmitted through the speed reducer 216 to the roller 217. Thus, when the preparation syringe 104 is mounted in the inner case 111, even in a state in which the identification code 104a is not in a position corresponding to the opening 111a, the identification code 104a can still be reliably read by the self-propelled code reader 112 when the preparation syringe 104 is rotated so that the identification code 104a appears in the opening 111a.

With the configurations in FIGS. 7 and 8 described in the above Embodiments 2 and 3, the electrical blocks and the operation flowchart are substantially the same as what was shown in FIGS. 5 and 6 and described in Embodiment 1 above. What is different is that the syringe drive motor 215 shown in FIGS. 7 and 8 is connected to motor drive circuit 120 in FIG. 5.

Embodiment 4

Figure 9:
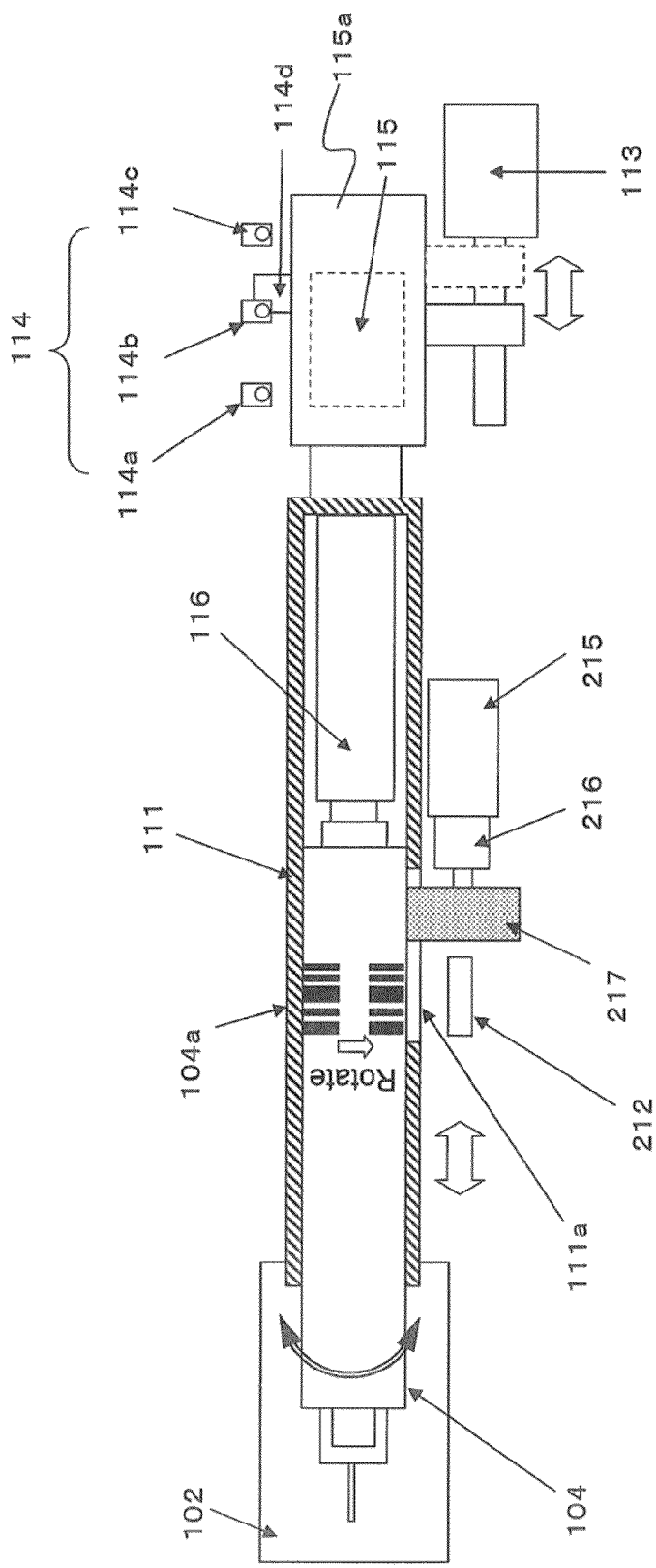
FIG. 9 is a cross section of the main components of the pharmaceutical injection device pertaining to Embodiment 4 of the present invention.

FIG. 9 shows the configuration of the pharmaceutical injection device pertaining to Embodiment 4 of the present invention. Here, the portions of the configuration shown in FIG. 9 that are the same as those in FIGS. 1 to 8 will be numbered the same and will not be described again.

Embodiment 4 is a combination of Embodiments 1 and 2 above, or of Embodiments 1 and 3.

Specifically, the configuration is such that the identification code 104a provided to the outer peripheral face of the preparation syringe 104 can be read whether it is disposed in the axial direction of the preparation syringe 104 or it is disposed in the outer peripheral direction.

In this case, the identification code 104a is read by the code reader 112 by moving the inner case 111 in the forward and backward direction (the left and right direction in FIG. 9) in the axial direction of the preparation syringe 104 under the drive of the slide motor 113.

If the identification code 104a is read successfully by this operation, thereafter injection is performed M the same manner as in Embodiment 1.

On the other hand, if the identification code 104a cannot be read in this state, the syringe drive motor 215 is driven to turn the preparation syringe 104 (in the up and down direction in FIG. 9), which is in contact with the roller 217 via the speed reducer 216. Consequently, even in a case such as this, the code reader 112 can be used to read the identification code 104a.

As discussed above, with this embodiment, the identification code 104a can be read regardless of the orientation of the identification code 104a provided to the outer peripheral face of the preparation syringe 104.

Embodiment 5

Figure 10:
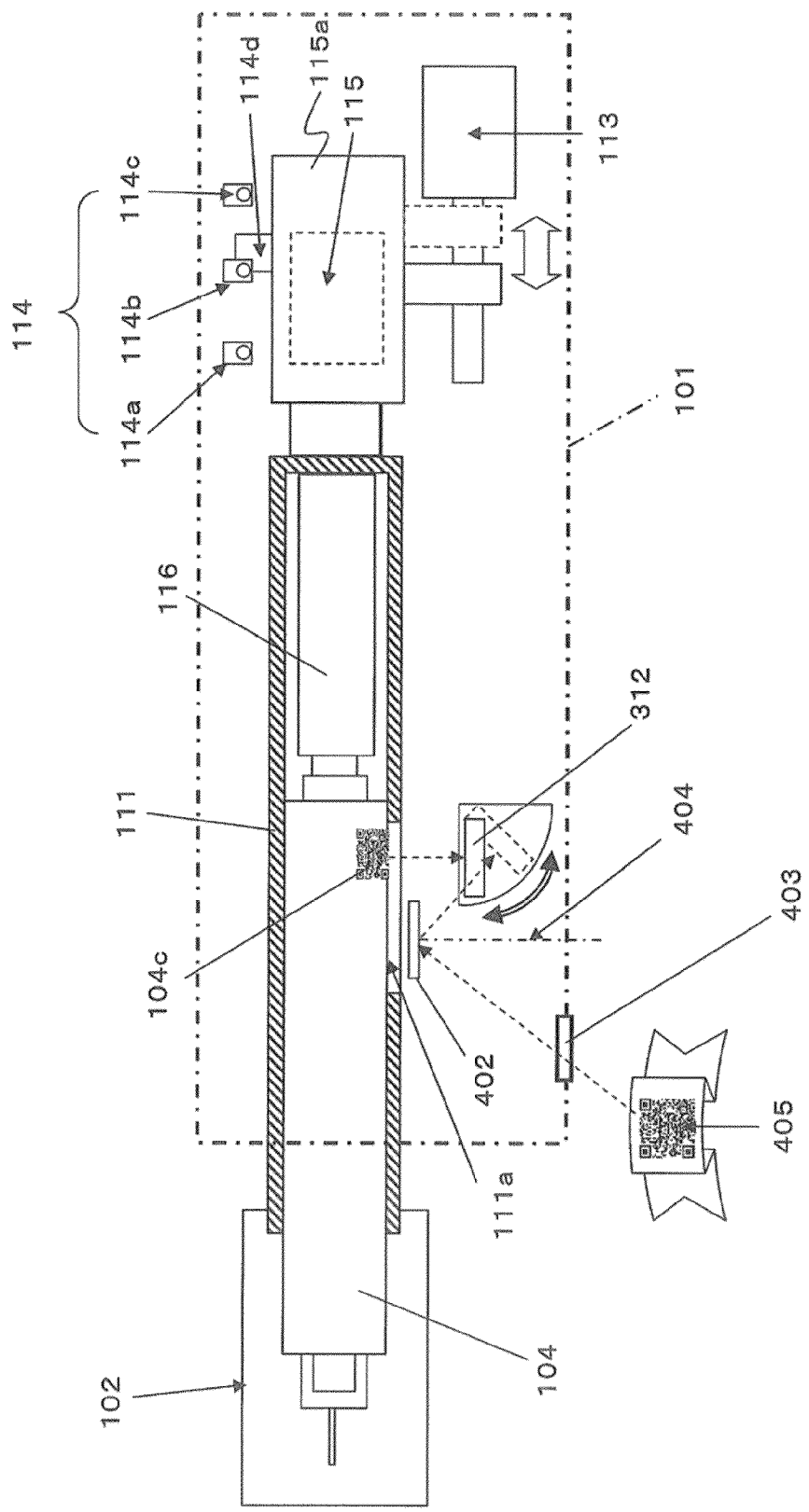
FIG. 10 is a cross section of the main components of the pharmaceutical injection device pertaining to Embodiment 5 of the present invention.

FIG. 10 shows the configuration of the pharmaceutical injection device pertaining to Embodiment 5 of the present invention. Here, the portions of the configuration shown in FIG. 10 that are the same as those in Embodiment 1 above will be numbered the same and will not be described again.

In this embodiment, QR code is used as the identification code 104c provided to the preparation syringe 104. This identification code 104c is read by a code reader 312 through the opening 111a.

As shown by the dashedline in FIG. 10 the code reader 312 has a structure that turns approximately 45 degrees. That is, in this embodiment, the code reader 312 reads the identification code 104c on the preparation syringe 104, and rather than just reading whether or not this is the proper syringe, an external identification code, such as an identification code 405 for a patient tag, can be read, for example.

Therefore, a reflector plate 402 is provided outside the opening 111a on the inside of the housing 101, and an opening 403 is newly provided to the part of the housing 101 (shown by the dotted line box) corresponding to an extension of the angle portion in symmetry with the code reader 112 that has moved as shown by the dashed line in the drawing, with respect to the center line 404 of this reflector plate 402.

That is, the code reader 312 can also read the identification code 405 placed outside the housing 101, through the reflector plate 402 and the opening 403, after turning approximately 45 degrees, as shown by the dashed line in the drawing.

To prevent dust and the like from getting into the housing 101, the opening 403 is preferably provided with a transparent plate (not shown) or the like.

Embodiment 6

Figure 11:
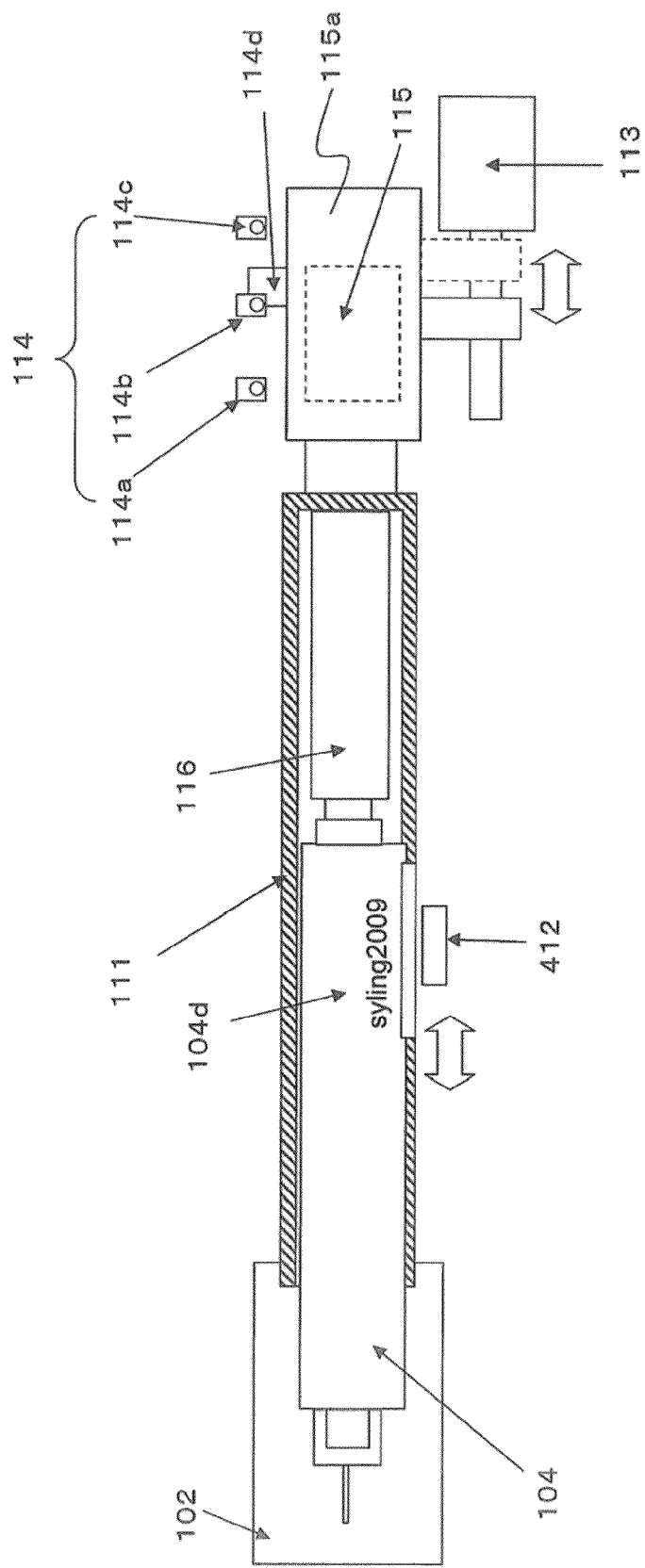
FIG. 11 is a cross section of the main components of the pharmaceutical injection device pertaining to Embodiment 6 of the present invention.

FIG. 11 shows the configuration of the pharmaceutical injection device pertaining to Embodiment 6 of the present invention. Here, the portions of the configuration shown in FIG. 11 that are the same as those in Embodiment 1 above will be numbered the same and will not be described again.

This embodiment differs from the above embodiments in that a character string is used as the identification code 104d provided to the outer peripheral face of the preparation syringe 104.

This character string may be printed directly on the preparation syringe 104, or a label printed with the character string may be affixed. However, taking into account the conditions for the identification code 104d, a label is more stable than an identification code printed directly. This is because if the preparation syringe 104 is made from transparent glass or another such material, there will be problems such as letting light through, or scattering and reflecting light since there is surface gloss. In view of this, the identification code 104d of this embodiment is preferably the product of printing a character string on an opaque label.

Therefore, an OCR (optical character reader) or another such device that can read the identification code 104d composed of a character string may be used, for example, as the code reader 412.

Embodiment 7

Figure 12:
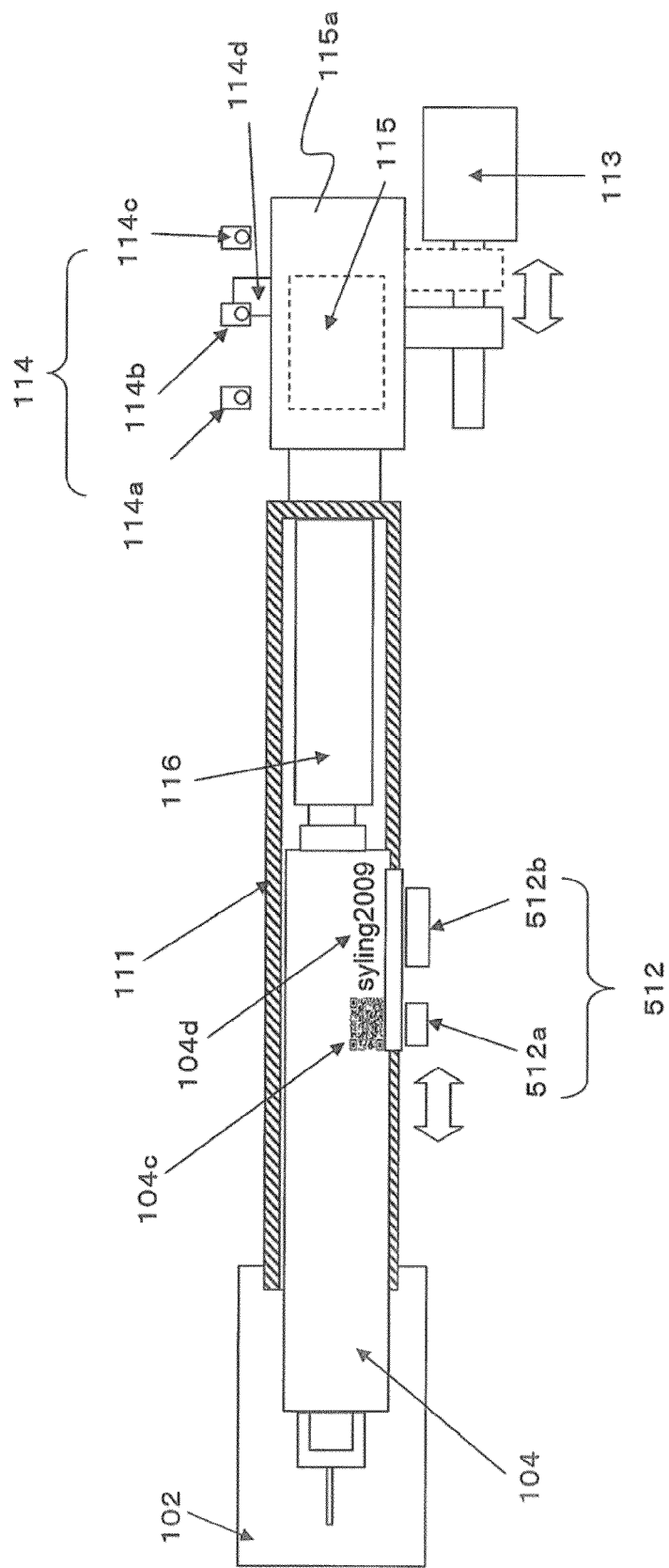
FIG. 12 is a cross section of the main components of the pharmaceutical injection device pertaining to Embodiment 7 of the present invention.

FIG. 12 shows the configuration of the pharmaceutical injection device pertaining to Embodiment 7 of the present invention. Here, the portions of the configuration shown in FIG. 12 that are the same as those in Embodiment 6 above will be numbered the same and will not be described again.

This embodiment differs from Embodiments 1 to 6 above in that an identification code 104d that is a character string and an identification code 104c that is QR code are provided to the outer peripheral face of the preparation syringe 104.

These identification codes 104c and 104d may be read by a single code reader, or the identification code 104c may be read by a code reader 512 and the identification code 104d by another code reader 512.

A QR code reader can be used as the one code reader 512, for example, and an OCR (optical character reader) or the like can be used as the other code reader 512.

When a single code reader is used, a CCD camera is used, for example, to capture images of the two identification codes, the identification code 104c is read and recognized with QR code reading software, and the identification code 104d with OCR software or the like.

Embodiment 8

The pharmaceutical injection device pertaining yet another embodiment of the present invention will now be described through reference to FIG. 13.

Figure 13:
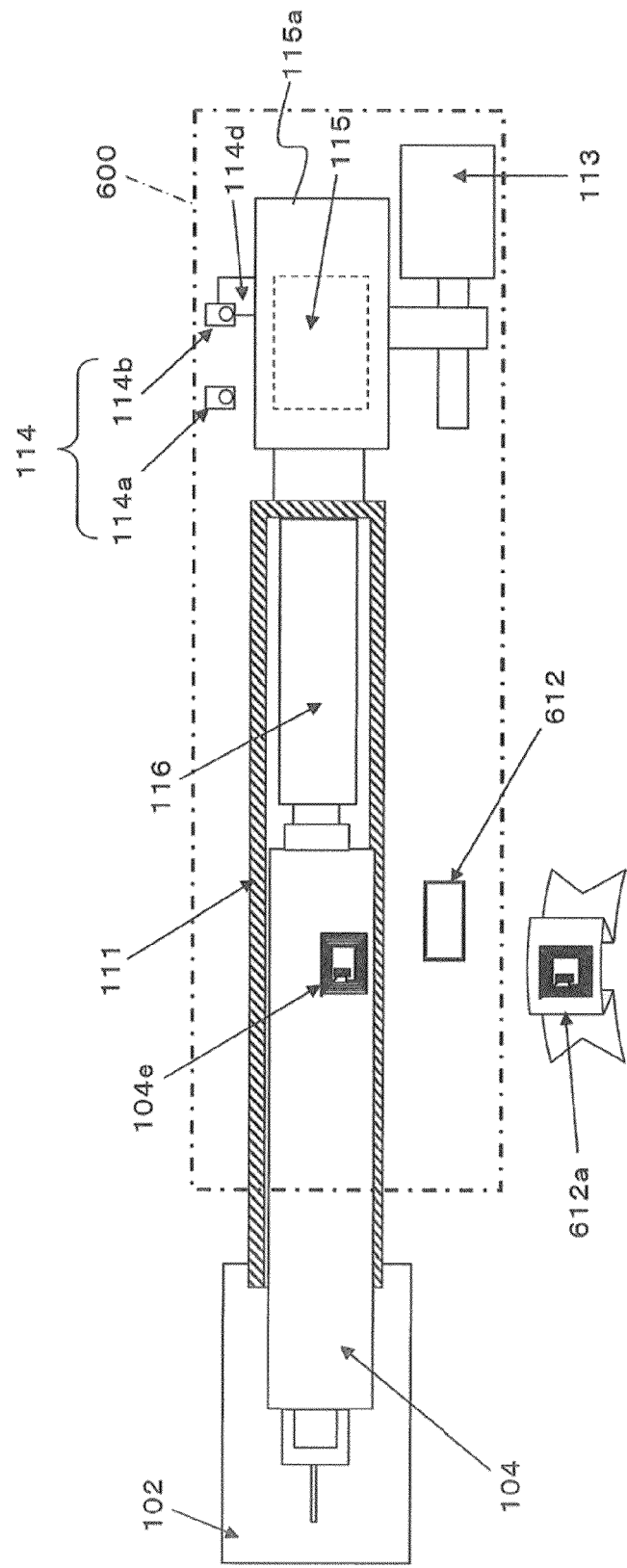
FIG. 13 is a cross section of the main components of the pharmaceutical injection device pertaining to Embodiment 8 of the present invention.

FIG. 13 shows the configuration of the pharmaceutical injection device pertaining to this embodiment. Here, the portions of the configuration shown in FIG. 13 that are the same as those in the above embodiments will be numbered the same and will not be described again.

This embodiment differs from the above embodiments in that RF-ID is used as an identification code 104e on the outer peripheral face of the preparation syringe 104, as shown in FIG. 13.

"RF-ID" (radio frequency-identification) here refers collectively to performing short-distance communication to read and write data from and to a semiconductor memory in non-contact fashion through an induction field or radio waves (see JIS X 0500: 2002).

RF-ID is used for the purpose of linking a person (carrying the ID) or object (to which the ID is attached) with information about the person or object. That is, required information can he taken out as needed at the place where the person or object is located, and new information can he written when necessary.

Types of RF-ID include a card type (SC17) or a tag type (SC31). Well known examples of card-type RF-ID include Silica, which is used in railway automatic turnstiles, Ikoca, and other such Felica cards. A tag type can be made in any shape desired, and examples include the IC tag used by hospital patients, and the IC tag used in distribution systems.

In this embodiment, a pharmaceutical injection device 600 comprises an RF-ID reader 612 as a code reader inside the main body (the portion enclosed by the dotted line in the drawing). When a preparation syringe 104 having the identification code 104e as an RF-ID is mounted to the device main body, the RF-ID reader 612 is used to read the identification code 104e of the preparation syringe 104, and determine whether or not the proper preparation syringe 104 has been mounted.

Since RF-ID is wireless, there is no need to operate motors as in Embodiments 1 to 7 above, so these will not be described here.

Whether or not the relation between a patient and the preparation syringe 104 mounted inside the device main body is the proper one can be determined by bringing the device main body close to a patient RF-ID tag 612a provided to the patient, and these affords greater safety.

Also, since RF-ID is wireless, the distance it reaches can be varied according to the built-in antenna or the frequency that is used. In this embodiment, a short-distance (such as 100 mm or less, and preferably 30 mm or less) type of tag is used. Consequently, when the RF-ID reader 612 is used to read the identification code, this prevents the unintended reading of the codes of other nearby preparation syringes or adjacent patients.

That is, the required information can be read and evaluated merely by bringing the device main body close to the object to be read whenever necessary.

As to the timing at which the RF-ID is read, more accurate reading can be performed by activating the system only when the preparation syringe 104 has been mounted to the main body of the pharmaceutical injection device 600 when he identification code (RF-ID) 104e of the preparation syringe 104 is read, and activating reading only when one of a variety of control buttons provided to the device main body has been pressed when the patient RF-ID tag 612a is read. A control button may be provided separately as an external read button, or other existing buttons (such as the finish button) may be used.

Since RF-ID is capable of both reading and writing, an "RF-ID reader/writer" (not shown) that can read and write RF-ID data can also be used instead of the RF-ID reader 612 shown in FIG. 8.

Because of this, data such as the number of injections with a preparation syringe 104, the injected dose, the date of injection (year, month, date, hour, minutes, seconds, etc.), and the remaining about of preparation can be recorded to the identification code (RF-ID) 104e of the preparation syringe 104. This eliminates problems with management of the preparation syringes, so more accurate management is possible.

Similarly, the number of times a patient has been injected with a pharmaceutical, the injected amount, the injection data (same as above), and other such injection history can be recorded at periodic intervals to the patient RF-ID tag 612a attached to this patient.

Naturally, data such as that mentioned above can also be recorded as history on the main body side of the pharmaceutical injection device 600, and this data can be put to good use in clinical treatment and in patient management.

In addition, data such as a patient's illness, body temperature, blood pressure, pulse rate, and glucose level is preferably recorded as patient data to the patient RF-ID tag 612a along with the dates (same as above) on which these measurements were made. In this case, when a pharmaceutical is injected with the pharmaceutical injection device 600, the latest information for that patient can be checked to determine whether or not it really is alright to inject the patient with that pharmaceutical. If there should be anything amiss in the patient data, a warning display can be given to notify the user, so that the data can be rechecked. As a result, more accurate pharmaceutical injection, including the patient's status, can be carried out.

Main Features

As discussed above, Embodiments 1 to 8 of the present invention are all the same in that it is possible to determine whether or not a preparation syringe 104 is the proper one can be determined after that preparation syringe 104 has been mounted in the inner case 111, by reading the identification code 104a to 104e with the code reader 112 Consequently, the identification code of the preparation syringe can be reliably read, so the result is a pharmaceutical injection device that is extremely convenient to use.

Specifically, when the determination is made at the point when the preparation syringe is mounted inside the inner case as with a conventional pharmaceutical injection device, since the mounting is performed by hand, it is more likely that the identification code will be incorrectly read. Furthermore, every time there is a reading mistake, the preparation syringe has to be remounted in the inner case, which is extremely inconvenient.

By contrast, with the pharmaceutical injection device pertaining to the present invention, the identification code 104a to 104e is read by the code reader 112 after the preparation syringe 104 has been mounted inside the inner case 111. Consequently, no misreading is caused by manual mounting, and as a result, there is no need for the mounting inside the inner case 111 to be repeated, so a pharmaceutical injection device that is extremely convenient to use can be obtained.

Industrial Applicability

The pharmaceutical injection device of the present invention does not require a preparation syringe to be remounted over and over to the mounting portion in order to read the identification code, so a pharmaceutical injection device that is extremely convenient to use can be obtained. As such, this pharmaceutical injection device is expected to find wide application in hospitals and by individuals.

Reference Signs List 100 pharmaceutical injection device
101 housing
102 distal end cap
102a distal end opening
103 confirmation window
104 preparation syringe
104a, 104b, 104c, 104d, 104e identification code
105 power button
106 air bleed button
107 finish button
108 pharmaceutical injection button
109 display section
110 injection needle
111 inner case
111a opening
112 code reader
113 slide motor
114 position detector
114a, 114b, 114c photosensor
114d blocker plate
115 piston drive motor
115a case
116 piston unit
117 encoder
118 current detection circuit
120 motor drive circuit
120b protrusion
121 microprocessor
123 sounding unit
124 vibrator
125 power supply
125a rechargeable battery
125b recharging circuit
126 memory
127 syringe detection switch
130 electrical circuit
150 dedicated cartridge
150a identification code
212 code reader
215 syringe drive motor
216 speed reducer
217 roller
312 code reader
402 reflector plate
403 opening
404 center line
405 patient tag identification code
412 code reader
512 code reader
600 pharmaceutical injection device
612 code reader
612a patient RF-ID tag

The invention claimed is:

1. A pharmaceutical injection device, comprising:
a mounting portion to which is mounted a preparation syringe having an identification code;
a piston unit that pushes out a pharmaceutical from the preparation syringe mounted to the mounting portion;
an injection driver that drives the piston unit;
a reading section that reads the identification code on the preparation syringe; and
a read driving section that drives the preparation syringe and/or the reading section, so that the identification code is read by the reading section.

2. The pharmaceutical injection device according to claim 1,
wherein the read driving section has a first read driving section that moves the preparation syringe mounted to the mounting portion in the axial direction of the preparation syringe.

3. The pharmaceutical injection device according to claim 1, further comprising:
a main body case that houses in its interior the mounting portion, the injection driver, the reading section, and the read driving section; and
an opening for the reading section, which is provided to the main body case.

4. The pharmaceutical injection device according to claim 3,
further comprising a transparent plate that is mounted in the opening.

5. The pharmaceutical injection device according to claim 1,
wherein the read driving section has a position detector that detects the position of the identification code.

6. The pharmaceutical injection device according to claim 1,
further comprising a notification section connected to the reading section, that conveys a reading result.

7. The pharmaceutical injection device according to claim 2, further comprising two photosensors which detect two positions of the mounting portion in the axial direction, respectively,
wherein the first read driving section moves the mounting portion for moving the preparation syringe mounted to the mounting portion,
and wherein the reading section reads the identification code while the mounting portion is reciprocated between the two positions by the first read driving section.

8. The pharmaceutical injection device according to claim 2, further comprising a driving section which drives the mounting portion for inserting an injection needle,
wherein the preparation syringe is configured such that the injection needle injecting the pharmaceutical in the preparation syringe is attached thereto,
wherein the first read driving section moves the mounting portion for moving the preparation syringe mounted to the mounting portion,
and wherein the driving section serves as the first read driving section.

9. The pharmaceutical injection device according to claim 3,
wherein the reading section is configured to turn between a first position and a second position, to read the identification code provided on the preparation syringe in the first position, and to read an identification code placed outside the main body case through the opening in the second position.

\* \* \* \* \*